United States Patent
Anraku et al.

(10) Patent No.: US 8,642,254 B2
(45) Date of Patent: Feb. 4, 2014

(54) COMPOSITION FOR SEPARATION OF SERUM OR PLASMA AND CONTAINER FOR BLOOD TEST

(75) Inventors: Hideo Anraku, Shunan (JP); Hiroaki Taira, Shunan (JP)

(73) Assignee: Sekisui Chemical Co., Ltd., Osaka (JP)

( * ) Notice: Subject to any disclaimer, the term of this patent is extended or adjusted under 35 U.S.C. 154(b) by 1098 days.

(21) Appl. No.: 12/302,146

(22) PCT Filed: May 25, 2007

(86) PCT No.: PCT/JP2007/060706
§ 371 (c)(1),
(2), (4) Date: Nov. 24, 2008

(87) PCT Pub. No.: WO2007/139018
PCT Pub. Date: Dec. 6, 2007

(65) Prior Publication Data
US 2009/0146099 A1      Jun. 11, 2009

(30) Foreign Application Priority Data

May 25, 2006    (JP) .................................. 2006-145557

(51) Int. Cl.
*A01N 1/02*      (2006.01)
*B01D 21/26*     (2006.01)
*G01N 31/00*     (2006.01)

(52) U.S. Cl.
USPC .................... 435/2; 210/516; 210/789; 436/8

(58) Field of Classification Search
None
See application file for complete search history.

(56) References Cited

U.S. PATENT DOCUMENTS

| 5,510,237 A | 4/1996 | Isogawa et al. |
| 7,090,970 B2 * | 8/2006 | Anraku et al. ............ 435/2 |
| 2004/0129631 A1 | 7/2004 | Anraku et al. |

FOREIGN PATENT DOCUMENTS

| EP | 0566794 A1 | 10/1993 |
| EP | 1452865 A1 | 9/2004 |
| JP | 64-006863 A | 1/1989 |
| JP | 04-337458 A | 11/1992 |
| JP | 06-003356 A | 1/1994 |
| JP | 06-324034 A | 11/1994 |
| JP | 09-015238 A | 1/1997 |
| WO | 03/048764 A1 | 6/2003 |

OTHER PUBLICATIONS

English translation of JP 64-006863, Jan. 11, 1989.*
Extended European Search Report mailed Jun. 17, 2009 in European Patent Application 07 744 140.0-1223.

* cited by examiner

*Primary Examiner* — Sandra Saucier
(74) *Attorney, Agent, or Firm* — Sughrue Mion, PLLC

(57) ABSTRACT

Disclosed is a composition for the separation of a serum or plasma, which comprises a cyclopentadiene oligomer, can be used for separating a serum or plasma by utilizing the difference in specific gravity among blood components, and enables to provide a serum or plasma having no oily component floating therein after centrifugal separation. The composition comprises a trimellitic acid ester and/or a pyromellitate ester and a cyclopentadiene oligomer. Alternatively, the composition comprises an aromatic esterified compound and a cyclopentadiene oligomer as the main ingredients and additionally comprises an inorganic micropowder and an organic gelling agent as thixotropy-imparting agents, wherein the organic gelling agent is contained in an amount of less than 0.06 parts by weight relative to 100 parts by weight of the cyclopentadiene oligomer.

5 Claims, 1 Drawing Sheet

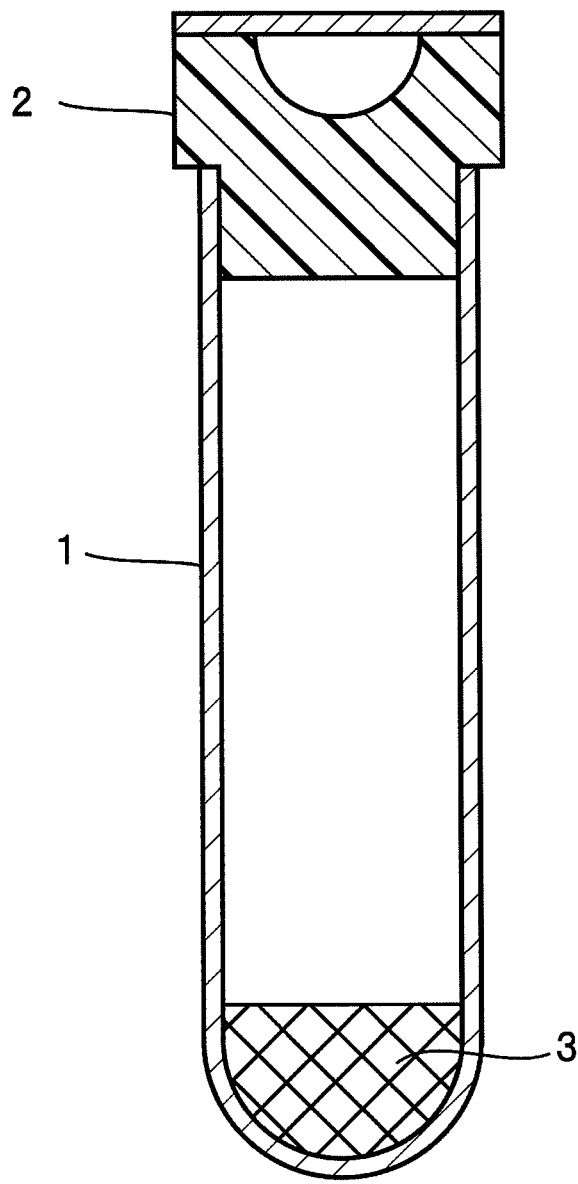

COMPOSITION FOR SEPARATION OF SERUM OR PLASMA AND CONTAINER FOR BLOOD TEST

TECHNICAL FIELD

The present invention relates to a composition used for separating a serum or a plasma from a blood, and to a container for blood tests. In more detail, the present invention relates to a composition for separating the serum or the plasma from the blood based on utilization of the difference in specific gravity between the blood components, and also relates to a container for blood tests.

BACKGROUND ART

Conventionally, quick separation of a serum or a plasma from a blood is strongly required in blood testing etc. Generally, there are widely used methods of using the difference in specific gravity between blood corpuscle components (specific gravity approximately 1.08), and a serum or a plasma (specific gravity approximately 1.03) in separation of the serum or the plasma from the blood. Then, in separation of the serum or the plasma using the difference in specific gravity, various compositions, having a specific gravity adjusted in a range of 1.03 to 1.08, more preferably in a range of 1.04 to 1.06, for separation of the serum or the plasma have been proposed for quicker and more reliable separation of the serum or the plasma, etc. from the blood corpuscle component.

As such compositions for separation of a serum or a plasma, following patent document 1 discloses a composition for separation based on the difference in the specific gravity including a hydrogenated cyclopentadiene petroleum resin as a cyclic hydrocarbon oligomer, and a phthalic acid ester that is an aromatic esterified compound. The patent document 1 describes that the composition enables detailed setting of a specific gravity value, has outstanding separative power as a separating medium utilizing the difference in the specific gravity, and further avoids deterioration by chemical change or moisture absorption.

However, the composition for separation by the difference in the specific gravity described in the patent document 1 has poor compatibility between the components constituting the composition, leading to frequent separation of oily components. Accordingly, the oily components separated are liable to float in the serum or the plasma after centrifugal separation. That is, the above-described oily components that float as impurities in the serum or the plasma might cause clogging of a sampling nozzle of an analysis apparatus, and trouble in blood testing by attaching to the surface of an electrolyte sensor.

Patent document 1: JP, 9-15238, A

DESCRIPTION OF THE INVENTION

Objects of the present invention are to provide a composition for separation of a serum or a plasma for providing solution to defects in the above-described conventional technology, the composition using the difference in the specific gravity of the blood components including cyclopentadiene oligomers, avoiding floating of oily components in the serum or the plasma after centrifugal separation, and to provide a container for the blood tests using the composition.

The composition for separation of the serum or the plasma in a first aspect concerning the present invention includes a trimellitic acid ester and/or a pyromellitic acid ester, and a cyclopentadiene oligomer.

The trimellitic acid ester and/or the pyromellitic acid ester are preferably blended at a proportion of 40 to 240 parts by weight to the cyclopentadiene oligomer 100 parts by weight.

The composition for separation of the serum or the plasma of a second aspect concerning the present invention includes an aromatic esterified compound and a cyclopentadiene oligomer as principal components, and an inorganic fine powder and an organic gelling agent as reagents for providing thixotropic property, the organic gelling agent being less than 0.06 parts by weight to the cyclopentadiene oligomer 100 parts by weight.

The container for the blood tests concerning the present invention comprises a container body, and the composition for separation of the serum or the plasma of the present invention stored in the container body.

Hereinafter, details of the present invention will be described.

The composition for separation of the serum or the plasma of the first aspect concerning the present invention includes the trimellitic acid ester and/or the pyromellitic acid ester, and the cyclopentadiene oligomer as essential components.

The above-described cyclopentadiene oligomer is not in particular limited, and cyclopentadiene oligomers having a softening point in a range of 70 to 140° C., and a specific gravity at 25° C. in a range of 1.00 to 1.10 may preferably be used. Furthermore, in order to allow easy adjustment of the specific gravity of the composition for separation of the serum or the plasma, the specific gravity at 25° C. of the above-described cyclopentadiene oligomer is more preferably in a range of 1.04 to 1.10.

The cyclopentadiene oligomers usable are not in particular limited, and examples of the oligomers include, for example, polymers of cyclopentadiene monomers, such as, hydrogenated compounds of polymers of at least one kind of monomers selected from alkyl substituted derivatives of cyclopentadiene, dicyclopentadiene, cyclopentadiene, etc. As such cyclopentadiene oligomers, for example, commercially available products made by TONEX Corporation currently mentioned as the trade name: ESCOREZ5000 series, that is, 5380 (softening point 85° C., specific gravity (25° C./4° C.) 1.07); 5300 (softening point 105° C., specific gravity (25° C./4° C.) 1.07); 5320 (softening point 125° C., specific gravity (25° C./4° C.) 1.07); 5340 (softening point 137° C., specific gravity (25° C./4° C.) 1.07); 5400 (softening point 102° C., specific gravity (25° C./4° C.) 1.07); ECR251 (softening point 103° C., specific gravity (25° C./4° C.) 1.07) etc. may be used.

In addition, hydrogenated copolymers obtained by at least one kind of the above-described cyclopentadiene monomers, and at least one kind of aromatic monomers selected from styrene, methyl styrene, indene, methyl indene, etc. may also be used. For example, commercially available items of ESCOREZ5000 series, that is, ECR227E (softening point 125° C., specific gravity (25° C./4° C.) 1.06); ECR235E (softening point 130° C., specific gravity (25° C./4° C.) 1.06); ECR231C (softening point 105° C., specific gravity (25° C./4° C.) 1.05); 5690 (softening point 90° C., specific gravity (25° C./4° C.) 1.06); 5600 (softening point 102° C., specific gravity (25° C./4° C.) 1.05) etc. may be used.

The composition for separation of the serum or the plasma of the present invention includes trimellitic acid esters and/or pyromellitic acid esters.

Trimellitic esters or pyromellitic acid esters to be used in the present invention belong to aromatic esterified compounds as well as phthalic acid esters, and they are not in particular limited as long as they are esters of trimellitic acid, or esters of pyromellitic acid. For example, alkylesters of trimellitic acid or pyromellitic acid, in detail, tri n-octyl trimellitate, tri iso-octyl trimellitate, tri iso-decyl trimellitate, tetra iso-octyl pyromellitate may be mentioned as trimellitic acid esters or pyromellitic acid esters.

Commercially available items of alkyl esters of the above-described trimellitic acid or pyromellitic acid include, for example, trade name: Monosizer W-700 (tri iso-octyl trimellitate, specific gravity (25° C./25° C.) 0.990, viscosity (25° C.) 220 mPa·s), Monosizer W-750 (tri n-octyl trimellitate, specific gravity (25° C./25° C.) 0.984, viscosity (25° C.) 93 mPa·s), Monosizer W-7010 (tetra-isooctyl pyromellitate, specific gravity (25° C./25° C.) 0.992, viscosity (25° C.) 460 mPa·s) manufactured by DIC Corporation; and trade name: manufactured by New Japan Chemical Co., Ltd. Sansosizer TOTM (tri iso-octyl trimellitate, specific gravity (20° C./4° C.) 0.990, viscosity (30° C.) 162 mPa·s), Sansosizer TITM (tri iso-decyl trimellitate, specific gravity (20° C./4° C.) 0.975, viscosity (30° C.) 287 mPa·s) etc.

Since the above-described trimellitic acid esters or pyromellitic acid esters have a larger numbers of lipophilic alkyl groups in molecule thereof as compared with the groups of phthalic acid esters, they may develop outstanding compatibility in combination with cyclopentadiene oligomers similarly having lipophilic property. Of trimellitic acid esters or pyromellitic acid esters, since tri n-octyl trimellitate and tri iso-octyl trimellitate have a specific gravity and a viscosity within particularly preferable ranges, these may preferably be used.

The above-described trimellitic acid ester and/or pyromellitic acid ester is preferably blended at a proportion of 40 to 240 parts by weight to the cyclopentadiene oligomer 100 parts by weight. Less than 40 parts by weight of the trimellitic acid ester and/or the pyromellitic acid ester excessively raises the viscosity of the blended material, leading to possible necessity of intense centrifugal force in separation of the serum or the plasma from the blood corpuscle component. In addition, exceeding 240 parts by weight of the trimellitic acid ester and/or the pyromellitic acid ester need charging of a large amount of inorganic fine powders for adjusting the specific gravity of the blended material to a value not less than 1.04, and therefore increases a yield value with time, leading to potential deterioration of septum formation property.

The trimellitic acid ester and/or the pyromellitic acid ester are more preferably blended at a proportion of 70 to 150 parts by weight to the cyclopentadiene oligomer 100 parts by weight.

Other various components in addition to the above-described essential component in an amount within a range that does not impair the objects of the present invention may be blended with the composition for separation of serum or plasma concerning the present invention. Such other components include inorganic fine powders and organic gelling agents as reagents for providing thixotropic property, inorganic fine powders as a specific gravity adjustment agent, polar organic solvents for gelation degree adjustment etc.

As the above-described organic gelling agents, for example, dibenzylidenesorbitol, bis(p-ethylbenzylidene)sorbitol, bis(p-methylbenzylidene)sorbitol, etc. may be mentioned as modified sorbitol compounds. Incidentally as the above-described inorganic fine powders, for example, fine powders, such as silica, kaolin, bentonite, alumina, synthetic silicate compounds, diatomaceous earth, etc. may be mentioned, irrespective of crystalline form, or noncrystalline form. Furthermore, as the above-described polar organic solvents, for example, acetone, dimethyl sulfoxide (DMSO), N-methylpyrrolidone (N-MP), ethylene glycol, propylene glycol, etc. may be mentioned. Any of them may be used independently, and may be used in combination.

In the composition for separation of the serum or the plasma of the second aspect concerning the present invention, the composition for separation of serum or plasma includes an aromatic esterified compound and a cyclopentadiene oligomer as principal components, and includes an inorganic fine powder and an organic gelling agent as reagents for providing thixotropic property, the organic gelling agent being less than 0.06 parts by weight to the cyclopentadiene oligomer 100 parts by weight.

The concentration of the organic gelling agent is preferably less than 0.04 parts by weight to the cyclopentadiene oligomer 100 parts by weight, and more preferably less than 0.02 parts by weight.

The aromatic esterified compound, the cyclopentadiene oligomer, the inorganic fine powder as reagents for providing thixotropic property, the organic gelling agent, etc. may be selected from the above-mentioned examples. Not less than 0.06 parts by weight of the concentration of the organic gelling agent to the cyclopentadiene oligomer 100 parts by weight may raise viscosity during preservation at room temperatures.

As a result, the above-mentioned phenomenon may not pose a large problem in case of larger centrifugal force and a higher temperature in centrifuge operation, but conversely the phenomenon may make formation of septum difficult in case of a smaller centrifugal force and a lower temperature in centrifuge operation.

However, it has been found out that the concentration of the organic gelling agent less than 0.06 parts by weight to the cyclopentadiene oligomer 100 parts by weight may demonstrate sufficient thixotropic property, and furthermore, may surprisingly suppress rise of viscosity during preservation at room temperatures, providing a composition for separation of serum or plasma having extremely high stability.

Reasons for the concentration of the organic gelling agent rising or suppressing the viscosity are yet unknown. It may probably be understood that in a condition of coexistence with the inorganic fine powder, the relationship between the thixotroping mechanism based on the interaction between the polar group of the organic gelling agent molecule, and the hydroxyl group of the surface of the inorganic fine powder and the thixotroping mechanism under respectively independent conditions may vary, bordering on a certain concentration.

Furthermore, the aromatic esterified compounds are preferably trimellitic acid ester and/or pyromellitic acid ester. Use of the trimellitic acid ester and/or the pyromellitic acid ester can suppress rise of viscosity, and further suppress separation of oily materials from the composition. Accordingly, floating of the separated oily component in the serum or the plasma after centrifugal separation may be avoided, and thereby trouble in the blood test by clogging of a sampling nozzle of an analysis apparatus and attaching to the surface of an electrolyte sensor will be avoided.

The container for the blood tests in accordance to the present invention stores the inventive composition for separation of serum or plasma in a container body. In this case, the shape of the container body is not in particular limited. For example, as illustrated in FIG. 1, the container body 1 etc. having various shape, for example, a tubular containers with a bottom that allow sealing with a plug 2, and that have conventionally been used for separation of the serum or the plasma may be used. In FIG. 1, the composition for separation of the serum or the plasma 3 is stored in the container.

Furthermore, materials constituting the container body are not in particular limited, but containers, for the blood tests, manufactured of glasses, synthetic resins, etc. may be used.

However, since they allow easy identification, by visual observation from the outside, of the separated serum or plasma, the containers for the blood tests are preferably manufactured using transparent materials.

In separation of the serum or the plasma from the blood using the composition for separation of the serum or the plasma concerning the present invention, for example, the composition for separation of the serum or the plasma is stored in the bottom of the above-described container for the blood tests, and subsequently the blood as a sample is stored in the container. Then, the container is to be subjected to centrifugal separation with a centrifugal separator. At this time, this centrifugation operation will precipitate solid contents in the blood downward, and will provide the serum or the plasma as a supernatant liquid. The composition for the separation forms a septum between both of the solid contents and the supernatant liquid. In addition, in the separation of the plasma, conventionally publicly known anticoagulants, such as K salts and Na salts of ethylenediamine tetra acetate are added beforehand in the blood and/or the container for the blood tests. Furthermore, in collecting the serum, the blood is collected into the container for the blood tests containing conventionally publicly known coagulation accelerators, for example, inorganic powders such as silica and diatomaceous earth, and serine proteases such as thrombins, etc. without use of the anticoagulant or instead of the anticoagulant. Subsequently, centrifugal separation is performed after the above-described coagulation.

EFFECT OF THE INVENTION

The composition for separation of the serum or the plasma concerning the first embodiment of the present invention includes a trimellitic acid ester and/or a pyromellitic acid ester, and a cyclopentadiene oligomer as essential components. Since the trimellitic acid ester and/or the pyromellitic acid ester, and the cyclopentadiene oligomer have excellent compatibility, it does not allow easy separation even in long term preservation. Accordingly, even in separation of the serum or the plasma using the container for the blood tests, after long term preservation, for storing the composition for separation of serum or plasma of the present invention, the serum or the plasma after centrifugal separation hardly allows floating of oily components.

The composition for separation of the serum or the plasma concerning the second embodiment of the present invention includes an aromatic esterified compound and a cyclopentadiene oligomer as principal components. Since the composition for separation of the serum or the plasma that includes an inorganic fine powder and an organic gelling agent as reagents for providing thixotropic property includes an organic gelling agent at a concentration less than 0.06 parts by weight with respect to the cyclopentadiene oligomer 100 parts by weight, the composition has a stable viscosity over a long period of time when kept standing at room temperatures, and therefore the capability for septum formation will be maintained for a long period of time.

Conventionally, the above described floating oily components sometimes gave clogging of a nozzle by the oily components and/or pollution of the surface of the electrolyte sensor by the oily components, in sampling of the serum or the plasma by a sampling nozzle after separation. On the contrary, since the present invention can reliably suppress mixing of the oily components to the serum or the plasma as described above, the present invention does not easily allow occurrence of troubles of a sampling nozzle, and furthermore does not allow pollution of the surface of the electrolyte sensor. Accordingly, use of the composition for separation of the serum or the plasma of the present invention enables reliable sampling of a clean serum or plasma from a blood.

Since the container for the blood tests of the present invention stores the composition for separation of serum or plasma of the above-described present invention, it allows reliable suppression of mixing of oily components to the serum or the plasma in sampling of the blood to the container for the blood tests, in centrifugal separation, and in collection of the serum or the plasma.

BRIEF DESCRIPTION OF THE DRAWINGS

FIG. 1 is a longitudinal sectional view of an example of the container for the blood tests of the present invention.

DESCRIPTION OF NOTATIONS

1—Container body
2—Plug
3—Composition for separation of serum or plasma

BEST MODE FOR CARRYING OUT THE INVENTION

Hereinafter, description of the present invention will be provided, with reference to detailed Examples and Comparative examples of the present invention.

The present invention is not limited to the following Examples.

Materials used in Examples and Comparative examples are shown as follows.

1) Cyclopentadiene oligomer: manufactured by Tonex Co., Ltd., trade name: ECR251, softening point 103° C., specific gravity (25° C./4° C.) 1.07;

2) Cyclopentadiene oligomer: manufactured by Tonex Co., Ltd., trade name: 5690, softening point 90° C., specific gravity (25° C./4° C.) 1.06;

3) Cyclopentadiene oligomer: manufactured by Tonex Co., Ltd., trade name: E5380, softening point 85° C., specific gravity (25° C./4° C.) 1.07;

4) Cyclopentadiene oligomer: manufactured by Tonex Co., Ltd., trade name: ECR231C, softening point 105° C., specific gravity (25° C./4° C.) 1.05;

5) Phthalic acid ester: used in Comparative example, manufactured by DIC Corporation, trade name: Mono-sizer DOP (dioctyl phthalate), specific gravity (20° C./20° C.) 0.986, viscosity (20° C.) 80 mPa·s;

6) Trimellitic ester: manufactured by DIC Corporation, trade name: Mono-sizer W-700 (tri iso-octyl trimellitate), specific gravity (25° C./25° C.) 0.990, viscosity (25° C.) 220 mPa·s;

7) Trimellitic ester: manufactured by DIC Corporation, trade name: Mono-sizer W-750 (tri n-octyl trimellitate), specific gravity (25° C./25° C.) 0.984, viscosity (25° C.) 93 mPa·s;

8) Organic gelling agent: dibenzylidenesorbitol (DBS), manufactured by New Japan Chemical Co., Ltd., and trade name: Gellall D;

9) Polar organic solvent: N-methylpyrrolidone (N-MP), reagent grade;

10) Fine powder silica: noncrystalline fine powder silica having a specific surface area of 250 $m^2/g$, manufactured by Tokuyama Corp., trade name: LEOLOSIL DM30S;

11) Fine powder silica: crystalline silica fine powder having an average particle diameter of about 3 micrometers, reagent grade;

12) Carbinol modified silicone oil: manufactured by Toray Dow Corning Corp., trade name: SF8427;
13) Polyvinyl pyrrolidone: PVP-K30, reagent grade;
14) Pyromellitic ester: manufactured by DIC Corporation, trade name: Mono-sizer W-7010 (tetra iso-octyl pyromellitate), specific gravity (25° C./25° C.) 0.992, viscosity (25° C.) 460 mPa·s;
15) Fine powder silica: noncrystalline fine powder silica having a specific surface area of 170 m²/g, manufactured by Japan Aerosil Co., Ltd., trade name: Aerosil R974; and
16) Fine powder silica: noncrystalline fine powder silica having a specific surface area of 200 m²/g, manufactured by Japan Aerosil Co., Ltd., trade name: Aerosil 200CF <Manufacture of a Composition for Separation of a Serum or a Plasma>

Following Table 1, Table 2, and Table 3 show the type of blended components used in Examples and Comparative examples, and the blending proportion (unit: parts by weight) of each blended components when the amount of cyclopentadiene oligomer is set as 100 parts by weight.

Into each of the trimellitic acid esters, the phthalic acid esters, or the pyromellitic acid ester that have been heated to 130 to 140° C. and agitated, the cyclopentadiene oligomer and the organic gelling agent, if necessary, were dissolved based at the blending proportion shown in Table 1 to Table 3. Subsequently, the mixture obtained were cooled to a room temperature about 25° C. to manufacture each composition for separation of the serum or the plasma. Here, the organic gelling agent was dissolved in a polar organic solvent for gelation degree adjustment for use. In the case of blending of the fine powder silica (noncrystalline), the fine powder silica was agitated and dispersed with a planetary mixer after cooling to a room temperature.

Following Table 1, Table 2, and Table 3 shows the types and the blending proportions of blended components used in Examples and Comparative examples, and the results of measurement of specific gravity (25° C./4° C.) of the compositions for separation of the serum or the plasma in Examples and Comparative examples.

TABLE 1

| | Trimellitic Acid Ester | | Phthalic Acid Ester | Cyclopentadiene Oligomer | | | | Gelling Agent | Gelation Degree Regulator | Fine Powder Silica | Specific Gravity |
|---|---|---|---|---|---|---|---|---|---|---|---|
| | W-700 | W-750 | DOP | ECR251 | E5380 | ECR231C | 5690 | GELLALL D | N-MP | DM30S | (25° C./4° C.) |
| Ex. 1 | 33 | | | | | | 100 | | | | 1.04 |
| Ex. 2 | 43 | | | | | | 100 | | | | 1.04 |
| Ex. 3 | 100 | | | | | | 100 | | | 8.3 | 1.05 |
| Ex. 4 | 100 | | | | | | 100 | 0.125 | 0.500 | 8.3 | 1.05 |
| Ex. 5 | 233 | | | | | | 100 | | | 22.0 | 1.05 |
| Ex. 6 | 300 | | | | | | 100 | | | 29.2 | 1.05 |
| Ex. 7 | | 33 | | 100 | | | | | | | 1.05 |
| Ex. 8 | | 43 | | 100 | | | | | | | 1.04 |
| Ex. 9 | | 100 | | 100 | | | | | | 8.3 | 1.05 |
| Ex. 10 | | 100 | | 100 | | | | 0.125 | 0.500 | 8.3 | 1.05 |
| Ex. 11 | | 233 | | 100 | | | | | | 22.4 | 1.04 |
| Ex. 12 | | 300 | | 100 | | | | | | 30.1 | 1.04 |
| Ex. 13 | 33 | | | | 100 | | | | | | 1.05 |
| Ex. 14 | 43 | | | | 100 | | | | | | 1.04 |
| Ex. 15 | 100 | | | | 100 | | | | | 8.3 | 1.05 |
| Ex. 16 | 100 | | | | 100 | | | 0.125 | 0.500 | 8.3 | 1.05 |
| Ex. 17 | 233 | | | | 100 | | | | | 22.0 | 1.05 |
| Ex. 18 | 300 | | | | 100 | | | | | 29.2 | 1.05 |
| Ex. 19 | | 33 | | | | 100 | | | | | 1.03 |
| Ex. 20 | | 43 | | | | 100 | | | | | 1.03 |
| Ex. 21 | | 100 | | | | 100 | | | | 8.3 | 1.04 |
| Ex. 22 | | 100 | | | | 100 | | 0.125 | 0.500 | 8.3 | 1.04 |
| Ex. 23 | | 233 | | | | 100 | | | | 22.4 | 1.04 |
| Ex. 24 | | 300 | | | | 100 | | | | 30.1 | 1.04 |
| Comp. Ex. 1 | | 100 | 100 | | | | | 0.125 | 0.500 | 8.3 | 1.05 |

TABLE 2

| | Pyromellitic Acid Ester | Low Molecular Weight Polyesters | Phthalic Acid Ester | Cyclopentadiene Oligomer | | | | Gelling Agent | Gelation Degree Regulator | Fine Powder Silica | Specific Gravity |
|---|---|---|---|---|---|---|---|---|---|---|---|
| | W7010 | W230H | DOP | ECR251 | E5380 | ECR231C | 5690 | GELLALL D | N-MP | DM30S | (25° C./4° C.) |
| Ex. 25 | 45 | | | | | 100 | | | | | 1.04 |
| Ex. 26 | 100 | | | | | 100 | | | | 6.0 | 1.05 |

TABLE 3

| | Trimellitic Acid Ester | | Phthalic Acid Ester | Cyclopentadiene Oligomer | | | | Gelling Agent | Gelation Degree Regulator | Fine Powder Silica | | | Specific Gravity |
|---|---|---|---|---|---|---|---|---|---|---|---|---|---|
| | W-700 | W-750 | DOP | ECR251 | E5380 | ECR231C | 5690 | GELLALL D | N-MP | DM30S | R974 | 200CF | (25° C./4° C.) |
| Ex. 27 | 90 | | | | 100 | | | 0.06000 | 0.240 | | 5.2 | 2.9 | 1.05 |
| Ex. 28 | 90 | | | | 100 | | | 0.04000 | 0.160 | | 5.2 | 2.9 | 1.05 |
| Ex. 29 | 90 | | | | 100 | | | 0.03000 | 0.120 | | 5.2 | 2.9 | 1.05 |
| Ex. 30 | 90 | | | | 100 | | | 0.02300 | 0.092 | | 5.2 | 2.9 | 1.05 |
| Ex. 31 | 90 | | | | 100 | | | 0.01900 | 0.076 | | 5.2 | 2.9 | 1.05 |
| Ex. 32 | 90 | | | | 100 | | | 0.01500 | 0.060 | | 5.2 | 2.9 | 1.05 |
| Ex. 33 | 90 | | | | 100 | | | 0.01200 | 0.048 | | 5.2 | 2.9 | 1.05 |
| Ex. 34 | 90 | | | | 100 | | | 0.00600 | 0.024 | | 5.2 | 2.9 | 1.05 |
| Ex. 35 | | | 80 | | | | 100 | 0.06000 | 0.240 | 8.1 | | | 1.05 |
| Ex. 36 | | | 80 | | | | 100 | 0.04000 | 0.160 | 8.1 | | | 1.05 |
| Ex. 37 | | | 80 | | | | 100 | 0.03000 | 0.120 | 8.1 | | | 1.05 |
| Ex. 38 | | | 80 | | | | 100 | 0.02300 | 0.092 | 8.1 | | | 1.05 |
| Ex. 39 | | | 80 | | | | 100 | 0.01900 | 0.076 | 8.1 | | | 1.05 |
| Ex. 40 | | | 80 | | | | 100 | 0.01500 | 0.060 | 8.1 | | | 1.05 |
| Ex. 41 | | | 80 | | | | 100 | 0.01200 | 0.048 | 8.1 | | | 1.05 |
| Ex. 42 | | | 80 | | | | 100 | 0.00600 | 0.024 | 8.1 | | | 1.05 |

<Manufacture of the Container for the Blood Tests for Storing the Composition for Separation of the Serum or the Plasma>

For each composition for separation of the serum or the plasma of Examples and Comparative examples, 20 containers for the blood tests were manufactured, respectively.

Each of the above-described compositions for separation of the serum or the plasma approximately 1.5 g was stored to each the bottom of 20 test tubes made of a polyethylene terephthalate having 7 mL of capacity. Onto the inner wall surface of the test tube, an aqueous suspension including a fine powder silica (average particle diameter of about 3 micrometers, crystalline) 2% by weight, a carbinol modified silicone oil 2% by weight, and polyvinyl pyrrolidone 2% by weight was sprayed at a proportion of about 20 mg/tube as a blood coagulation accelerator. Subsequently, each test tube was dried to obtain containers for the blood tests <Evaluation>

Of 20 of the manufactured containers for the blood tests, 10 containers for the blood tests were preserved for one week at room temperature of about 25° C. The remaining 10 containers for the blood tests were preserved for three months at room temperature of about 25° C.

After preservation as described above, 3 mL/container of a fresh human blood of a volunteer test subject was collected into each container for the blood tests. After completion of the blood coagulation, samples of Examples 1 to 42 and Comparative example 1 was centrifugally separated at 1300 G (for about 25° C. and 5 minutes). The separated condition of the serum and the clot component (septum formation) with a separating medium septum formed by the centrifugal separation, existence of hemolysis, and existence of floating of oily components were evaluated for by visual observation. At this point of time, the sample that gave imperfect septum formation was subjected to additional centrifugal separation at 1600 G (for about 25° C. and 5 minutes) for the same visual observation as mentioned above.

Samples of Examples 27 to 42 were centrifugally separated at 900 G (for about 15° C. and 5 minutes).

The separated condition of the serum and the clot component (septum formation) with a separating medium septum formed by the centrifugal separation, existence of hemolysis, and existence of floating of oily components were evaluated for by visual observation. At this point of time, the sample that gave imperfect septum formation was subjected to additional centrifugal separation at 1100 G (for about 15° C. and 5 minutes) for the same visual observation as mentioned above.

Following Table 4 and Table 5, and Table 6 show evaluation results of the composition for separation of the serum or the plasma of Examples and Comparative examples.

TABLE 4

Preservation Conditions
About 25° C. Room Temperature, One Week
Centrifuge Condition

| | 1300 G (25° C., 5 min.) | | | 1600 G (25° C., 5 min.) | | |
|---|---|---|---|---|---|---|
| | Observation Item | | | | | |
| | Septum Formation | Hemolysis Observed | Oily Component | Septum Formation | Hemolysis Observed | Oily Component |
| Ex. 1 | Almost Satisfactory | 0/5 | 0/5 | Satisfactory | 0/5 | 0/5 |
| Ex. 2 | Satisfactory | 0/5 | 0/5 | | | |
| Ex. 3 | Satisfactory | 0/5 | 0/5 | | | |
| Ex. 4 | Satisfactory | 0/5 | 0/5 | | | |
| Ex. 5 | Satisfactory | 0/5 | 0/5 | | | |
| Ex. 6 | Almost Satisfactory | 0/5 | 0/5 | Satisfactory | 0/5 | 0/5 |
| Ex. 7 | Almost Satisfactory | 0/5 | 0/5 | Satisfactory | 0/5 | 0/5 |
| Ex. 8 | Satisfactory | 0/5 | 0/5 | | | |
| Ex. 9 | Satisfactory | 0/5 | 0/5 | | | |
| Ex. 10 | Satisfactory | 0/5 | 0/5 | | | |
| Ex. 11 | Satisfactory | 0/5 | 0/5 | | | |
| Ex. 12 | Almost Satisfactory | 0/5 | 0/5 | Satisfactory | 0/5 | 0/5 |

TABLE 4-continued

| | | | | | | |
|---|---|---|---|---|---|---|
| Ex. 13 | Almost Satisfactory | 0/5 | 0/5 | Satisfactory | 0/5 | 0/5 |
| Ex. 14 | Satisfactory | 0/5 | 0/5 | | | |
| Ex. 15 | Satisfactory | 0/5 | 0/5 | | | |
| Ex. 16 | Satisfactory | 0/5 | 0/5 | | | |
| Ex. 17 | Satisfactory | 0/5 | 0/5 | | | |
| Ex. 18 | Almost Satisfactory | 0/5 | 0/5 | Satisfactory | 0/5 | 0/5 |
| Ex. 19 | Almost Satisfactory | 0/5 | 0/5 | Satisfactory | 0/5 | 0/5 |
| Ex. 20 | Satisfactory | 0/5 | 0/5 | | | |
| Ex. 21 | Satisfactory | 0/5 | 0/5 | | | |
| Ex. 22 | Satisfactory | 0/5 | 0/5 | | | |
| Ex. 23 | Satisfactory | 0/5 | 0/5 | | | |
| Ex. 24 | Almost Satisfactory | 0/5 | 0/5 | Satisfactory | 0/5 | 0/5 |
| Comp. Ex. 1 | Satisfactory | 0/5 | 0/5 | | | |

Preservation Conditions
About 25° C. Room Temperature, 3 Months
Centrifuge Condition

| | 1300 G (25° C., 5 min.) | | | 1600 G (25° C., 5 min.) | | |
|---|---|---|---|---|---|---|
| | Observation Item | | | | | |
| | Septum Formation | Hemolysis Observed | Oily Component | Septum Formation | Hemolysis Observed | Oily Component |
| Ex. 1 | Thin | 0/5 | 0/5 | Satisfactory | 0/5 | 0/5 |
| Ex. 2 | Satisfactory | 0/5 | 0/5 | | | |
| Ex. 3 | Satisfactory | 0/5 | 0/5 | | | |
| Ex. 4 | Satisfactory | 0/5 | 0/5 | | | |
| Ex. 5 | Thin | 0/5 | 0/5 | Satisfactory | 0/5 | 0/5 |
| Ex. 6 | Imperfect | 0/5 | 0/5 | Thin | 0/5 | 0/5 |
| Ex. 7 | Thin | 0/5 | 0/5 | Satisfactory | 0/5 | 0/5 |
| Ex. 8 | Satisfactory | 0/5 | 0/5 | | | |
| Ex. 9 | Satisfactory | 0/5 | 0/5 | | | |
| Ex. 10 | Satisfactory | 0/5 | 0/5 | | | |
| Ex. 11 | Thin | 0/5 | 0/5 | Satisfactory | 0/5 | 0/5 |
| Ex. 12 | Imperfect | 0/5 | 0/5 | Thin | 0/5 | 0/5 |
| Ex. 13 | Thin | 0/5 | 0/5 | Satisfactory | 0/5 | 0/5 |
| Ex. 14 | Satisfactory | 0/5 | 0/5 | | | |
| Ex. 15 | Satisfactory | 0/5 | 0/5 | | | |
| Ex. 16 | Satisfactory | 0/5 | 0/5 | | | |
| Ex. 17 | Thin | 0/5 | 0/5 | Satisfactory | 0/5 | 0/5 |
| Ex. 18 | Imperfect | 0/5 | 0/5 | Thin | 0/5 | 0/5 |
| Ex. 19 | Thin | 0/5 | 0/5 | Satisfactory | 0/5 | 0/5 |
| Ex. 20 | Satisfactory | 0/5 | 0/5 | | | |
| Ex. 21 | Satisfactory | 0/5 | 0/5 | | | |
| Ex. 22 | Satisfactory | 0/5 | 0/5 | | | |
| Ex. 23 | Thin | 0/5 | 0/5 | Satisfactory | 0/5 | 0/5 |
| Ex. 24 | Imperfect | 0/5 | 0/5 | Thin | 0/5 | 0/5 |
| Comp. Ex. 1 | Satisfactory | 0/5 | 3/5 | | | |

TABLE 5

Preservation Conditions
About 25° C. Room Temperature, One Week
Centrifuge Condition

| | 1300 G (25° C., 5 min.) | | | 1600 G (25° C., 5 min.) | | |
|---|---|---|---|---|---|---|
| | Observation Item | | | | | |
| | Septum Formation | Hemolysis Observed | Oily Component | Septum Formation | Hemolysis Observed | Oily Component |
| Ex. 25 | Thin | | 0/5 | Slightly Thin | 0/5 | 0/5 |
| Ex. 26 | Almost Satisfactory | 0/5 | 0/5 | Satisfactory | 0/5 | 0/5 |
| Ex. 27 | Satisfactory | 0/5 | 0/5 | | | |
| Ex. 28 | Satisfactory | 0/5 | 0/5 | | | |
| Ex. 29 | Satisfactory | 0/5 | 0/5 | | | |
| Ex. 30 | Satisfactory | 0/5 | 0/5 | | | |
| Ex. 31 | Satisfactory | 0/5 | 0/5 | | | |
| Ex. 32 | Satisfactory | 0/5 | 0/5 | | | |
| Ex. 33 | Satisfactory | 0/5 | 0/5 | | | |
| Ex. 34 | Satisfactory | 0/5 | 0/5 | | | |
| Ex. 35 | Satisfactory | 0/5 | 0/5 | | | |
| Ex. 36 | Satisfactory | 0/5 | 0/5 | | | |
| Ex. 37 | Satisfactory | 0/5 | 0/5 | | | |
| Ex. 38 | Satisfactory | 0/5 | 0/5 | | | |
| Ex. 39 | Satisfactory | 0/5 | 0/5 | | | |

TABLE 5-continued

| | | | |
|---|---|---|---|
| Ex. 40 | Satisfactory | 0/5 | 0/5 |
| Ex. 41 | Satisfactory | 0/5 | 0/5 |
| Ex. 42 | Satisfactory | 0/5 | 0/5 |

| | Preservation Conditions About 25° C. Room Temperature, 3 Months Centrifuge Condition | | | | | |
|---|---|---|---|---|---|---|
| | 1300 G (25° C., 5 min.) | | | 1600 G (25° C., 5 min.) | | |
| | Observation Item | | | | | |
| | Septum Formation | Hemolysis Observed | Oily Component | Septum Formation | Hemolysis Observed | Oily Component |
| Ex. 25 | Thin | 0/5 | 0/5 | Slightly Thin | 0/5 | 0/5 |
| Ex. 26 | Thin | 0/5 | 0/5 | Almost Satisfactory | 0/5 | 0/5 |
| Ex. 27 | Satisfactory | 0/5 | 0/5 | | | |
| Ex. 28 | Satisfactory | 0/5 | 0/5 | | | |
| Ex. 29 | Satisfactory | 0/5 | 0/5 | | | |
| Ex. 30 | Satisfactory | 0/5 | 0/5 | | | |
| Ex. 31 | Satisfactory | 0/5 | 0/5 | | | |
| Ex. 32 | Satisfactory | 0/5 | 0/5 | | | |
| Ex. 33 | Satisfactory | 0/5 | 0/5 | | | |
| Ex. 34 | Satisfactory | 0/5 | 0/5 | | | |
| Ex. 35 | Satisfactory | 0/5 | 0/5 | | | |
| Ex. 36 | Satisfactory | 0/5 | 0/5 | | | |
| Ex. 37 | Satisfactory | 0/5 | 0/5 | | | |
| Ex. 38 | Satisfactory | 0/5 | 0/5 | | | |
| Ex. 39 | Satisfactory | 0/5 | 0/5 | | | |
| Ex. 40 | Satisfactory | 0/5 | 0/5 | | | |
| Ex. 41 | Satisfactory | 0/5 | 0/5 | | | |
| Ex. 42 | Satisfactory | 0/5 | 0/5 | | | |

TABLE 6

| | Preservation Conditions About 25° C. Room Temperature, One Week Centrifuge Condition | | | | | |
|---|---|---|---|---|---|---|
| | 900 G (15° C., 5 min.) | | | 1100 G (15° C., 5 min) | | |
| | Observation Item | | | | | |
| | Septum Formation | Hemolysis Observed | Oily Component | Septum Formation | Hemolysis Observed | Oily Component |
| Ex. 27 | Satisfactory | 0/5 | 0/5 | | | |
| Ex. 28 | Satisfactory | 0/5 | 0/5 | | | |
| Ex. 29 | Satisfactory | 0/5 | 0/5 | | | |
| Ex. 30 | Satisfactory | 0/5 | 0/5 | | | |
| Ex. 31 | Satisfactory | 0/5 | 0/5 | | | |
| Ex. 32 | Satisfactory | 0/5 | 0/5 | | | |
| Ex. 33 | Satisfactory | 0/5 | 0/5 | | | |
| Ex. 34 | Satisfactory | 0/5 | 0/5 | | | |
| Ex. 35 | Satisfactory | 0/5 | 0/5 | | | |
| Ex. 36 | Satisfactory | 0/5 | 0/5 | | | |
| Ex. 37 | Satisfactory | 0/5 | 0/5 | | | |
| Ex. 38 | Satisfactory | 0/5 | 0/5 | | | |
| Ex. 39 | Satisfactory | 0/5 | 0/5 | | | |
| Ex. 40 | Satisfactory | 0/5 | 0/5 | | | |
| Ex. 41 | Satisfactory | 0/5 | 0/5 | | | |
| Ex. 42 | Satisfactory | 0/5 | 0/5 | | | |

| | Preservation Conditions About 25° C. Room Temperature, 3 Months Centrifuge Condition | | | | | |
|---|---|---|---|---|---|---|
| | 900 G (15° C., 5 min.) | | | 1100 G (15° C., 5 min) | | |
| | Observation Item | | | | | |
| | Septum Formation | Hemolysis Observed | Oily Component | Septum Formation | Hemolysis Observed | Oily Component |
| Ex. 27 | Thin | 0/5 | 0/5 | Thin | 0/5 | 0/5 |
| Ex. 28 | Thin | 0/5 | 0/5 | Almost Satisfactory | 0/5 | 0/5 |
| Ex. 29 | Thin | 0/5 | 0/5 | Almost | 0/5 | 0/5 |

TABLE 6-continued

| | | | | | | |
|---|---|---|---|---|---|---|
| Ex. 30 | Thin | 0/5 | 0/5 | Satisfactory Almost Satisfactory | 0/5 | 0/5 |
| Ex. 31 | Satisfactory | 0/5 | 0/5 | | | |
| Ex. 32 | Satisfactory | 0/5 | 0/5 | | | |
| Ex. 33 | Satisfactory | 0/5 | 0/5 | | | |
| Ex. 34 | Satisfactory | 0/5 | 0/5 | | | |
| Ex. 35 | Thin | 0/5 | 1/5 | Thin | 0/5 | 1/5 |
| Ex. 36 | Thin | 0/5 | 0/5 | Almost Satisfactory | 0/5 | 0/5 |
| Ex. 37 | Thin | 0/5 | 1/5 | Almost Satisfactory | 0/5 | 0/5 |
| Ex. 38 | Thin | 0/5 | 0/5 | Almost Satisfactory | 0/5 | 0/5 |
| Ex. 39 | Satisfactory | 0/5 | 0/5 | | | |
| Ex. 40 | Satisfactory | 0/5 | 1/5 | | | |
| Ex. 41 | Satisfactory | 0/5 | 0/5 | | | |
| Ex. 42 | Satisfactory | 0/5 | 0/5 | | | |

On one hand, in the composition for separation of the serum or the plasma of Comparative example using Monosizer DOP of phthalic acid ester, the container for the blood tests preserved for three months at room temperature of about 25° C. gave an oily component observed after centrifugal separation of 1600 G. On the other hand, however, the compositions for separation of serum or plasma of Examples 1 to 34 gave no oily components observed in all preservation conditions.

On one hand, the concentration of the organic gelling agent exceeding 0.06 parts by weight to the cyclopentadiene oligomer 100 parts by weight showed a tendency for septum formation property to decrease after three months at room temperature, under conditions of a low temperature of 15° C. and a low centrifugal force of 900 to 1100 G in Examples 27 to 42. On the other hand, the concentration less than 0.06 parts by weight showed stable septum formation.

What is claimed is:

1. A composition for separating serum or plasma from blood, wherein said composition comprises a cyclopentadiene oligomer and at least one ester selected from the group consisting of a trimellitic acid ester and a pyromellitic acid ester; wherein the cyclopentadiene oligomer has a specific gravity at 25° C. of 1.04 to 1.10.

2. The composition of claim 1, wherein said ester is present in said composition in an amount of 40 to 240 parts by weight with respect to 100 parts by weight of the cyclopentadiene oligomer.

3. A container for separating serum or plasma from blood, comprising a container body with the composition of claim 1 or 2 deposited therein.

4. A composition for separating serum or plasma from blood, wherein said composition comprises an aromatic esterified compound selected from the group consisting of a trimellitic acid ester and a pyromellitic acid ester, a cyclopentadiene oligomer, an inorganic fine powder and an organic gelling agent, wherein said organic gelling agent is present in said composition in an amount less than 0.06 parts by weight with respect to 100 parts by weight of the cyclopentadiene oligomer; wherein the cyclopentadiene oligomer has a specific gravity at 25° C. of 1.04 to 1.10.

5. A container for separating serum or plasma from blood comprising a container body with the composition of claim 4 deposited therein.

* * * * *